United States Patent [19]

Grollier et al.

[11] Patent Number: 4,566,875
[45] Date of Patent: Jan. 28, 1986

[54] TWO-STAGE PROCESS FOR DYEING KERATIN FIBRES AND COMPOSITION FOR USE THEREIN

[75] Inventors: Jean F. Grollier; Chantal Fourcadier, both of Paris, France

[73] Assignee: L'Oreal, Paris, France

[21] Appl. No.: 27,400

[22] Filed: Apr. 5, 1979

[30] Foreign Application Priority Data

Apr. 6, 1978 [FR] France ................ 78 10276

[51] Int. Cl.$^4$ .................. A45D 7/00; A61K 7/13; D06P 5/00
[52] U.S. Cl. .................. 8/406; 8/408; 8/409; 8/410; 8/411; 8/412; 8/478; 8/529; 8/638; 132/7
[58] Field of Search ............ 8/408, 478, 529, 638, 8/410, 411, 412, 409; 132/7

[56] References Cited

U.S. PATENT DOCUMENTS 2,101,696  12/1935  Wagner et al. ................ 8/478

FOREIGN PATENT DOCUMENTS

| 951538 | 4/1949 | France | 8/408 |
|---|---|---|---|
| 1036111 | 4/1953 | France | 8/408 |
| 1067850 | 2/1954 | France | 8/408 |
| 65506 | 10/1955 | France | 8/408 |
| 1257394 | 2/1961 | France | 8/408 |
| 2134003 | 1/1972 | France | 8/408 |
| 2252841 | 6/1975 | France | 8/408 |
| 1010973 | 1/1965 | United Kingdom | 8/408 |
| 1276771 | 8/1969 | United Kingdom | 8/408 |
| 1460952 | 1/1977 | United Kingdom | 8/408 |
| 1476239 | 6/1977 | United Kingdom | 8/408 |

*Primary Examiner*—Dale R. Ore
*Attorney, Agent, or Firm*—Fleit, Jacobson, Cohn & Price

[57] ABSTRACT

A two-stage process for dyeing keratin fibres, especially human hair, which comprises applying a first composition containing at least one mercaptan present in a concentration insufficient to causes degradation of the hair and subsequently without intermediate rinsing, applying an oxidising composition so as to develop the dyestuff, and optionally one or more couplers, which is applied to the fibres, the dyestuff being an oxidative dyestuff precursor of the para type, a diphenylamine, a polyhydroxybenzene, a polyhydroxynaphthalene, a polyaminobenzene, a polyaminophenol or a polyaminopolyhydroxybenzene is described and compositions for use therein.

7 Claims, No Drawings

TWO-STAGE PROCESS FOR DYEING KERATIN FIBRES AND COMPOSITION FOR USE THEREIN

The present invention relates to compositions which are intended for use in dyeing keratin fibres, and in particular in dyeing hair, especially human hair, and to a hair dyeing process employing this composition.

It is well known to colour keratin fibres, and in particular human hair, with oxidisable dyestuffs.

Oxidisable dyestuffs, as used herein, are the so-called oxidative dyestuffs, diphenylamines and dyestuffs for rapid oxidation.

Aromatic compounds of the diamine, aminophenol or phenol type are referred to as oxidative dyestuffs. These compounds, which are not in themselves dyestuffs, are converted into dyestuffs by a process of oxidative condensation.

Amongst these oxidative dyestuffs, there are on the one hand, the oxidative dyestuff precursors of the para type, which are generally diamines or aminophenols in which functional groups are located in the para-position relative to one another, and the oxidative dyestuff precursors of the ortho type which are usually diamines or aminophenols in which the functional groups are located in the ortho position relative to one another, and, on the other hand, modifying compounds or couplers which are so-called "meta derivatives" and are generally meta-diamines, m-aminophenols, m-diphenols as well as phenols.

The diphenylamines are generally leuco derivatives of indamines, indophenols and indoanilines, which are dyestuffs formed by condensing bases which the couplers described above.

Oxidative dyestuffs of the polyphenol, polyaminobenzene, polyaminophenol or polyaminopolyhydroxybenzene type, which are compounds capable of oxidising directly and rapidly in the air, are referred to as dyestuffs for rapid oxidation. Amongst these compounds, there may be mentioned, in particular, triaminobenzenes, di- or tri-aminophenols, diaminophenols in which the amino groups can optionally be substituted, and trihydroxy-benzenes or -naphthalenes which can be substituted on the nucleus (or nuclei).

These various oxidisable dyestuffs are generally applied to the hair by means of a dyeing composition, which contains an oxidising agent added to the said composition just before application in the case of oxidative dyestuffs and diphenylamines, whereas, if the composition contains dyestuffs for rapid oxidation or certain diphenylamines, it is usually applied, without oxidising agent, directly to the hair, the oxygen in the air causing the development of the dyestuffs.

However, the use of these oxidisable dyestuffs exhibits a certain number of disadvantages from the point of view of the dyeing effect obtained or of the amount of dyestuff required.

Thus, when they are applied to natural hair, certain oxidisable dyestuffs lack strength and are selective. In fact, in particular in the case of highly hindered oxidisable dyestuffs, uneven absorption of the dyestuff is observed and this manifests itself in a lack of final uniformity.

This uneven absorption is due, in particular, to the interaction of the keratin fibre with the dyestuffs, and this can vary from person to person but also over one and the same strand of hair. In fact, it is well known that the sensitisation of hair varies from point to point; that is to say it can be zero for a freshly grown root; it can be high for the parts which have previously been treated by colouring, bleaching or permanent waving and it can be very high for the parts such as, for example, the tips which have undergone several treatments and which are exposed daily to the action of light and harsh weather conditions.

This uneven or insufficient absorption of the dyestuffs on the hair can be explained, inter alia, by the structure of the reactants, or of the dyestuff molecules resulting from their condensation, which can be sterically hindered and thus be too bulky to penetrate the fibre.

This is particularly important in the case of the bulky or hindered oxidisable dyestuffs having high oxidation-reduction potentials and rapid oxidation kinetics, the consequence of which is that these dyestuffs rapidly form, in the dyeing carrier, and before these compounds are applied to the hair, compounds of large size which have difficulty in penetrating the fibre.

Furthermore, it is desirable to use these oxidisable dyestuffs in as small amounts as possible, with the result that it is desirable to exploit the colouring potential of this type of compound to the maximum extent.

Mercaptans are well known and have previously been recommended for permanently waving the head of hair and as antioxidants in dyeing compositions.

Such mercaptans have already been used in compositions combining the permanent waving and the dyeing of the hair, especially in the case of dyeing compositions containing direct dyestuffs, in particular acidic or metallised dyestuffs, and also certain oxidative dyestuffs.

However, the compositions intended for carrying out permanent waving and dyeing of the hair exhibit disadvantages arising, in particular, from the amount of mercaptan required to achieve permanent waving, which amount is generally between 5 and 7% by weight. The large amount of mercaptan in these compositions can have adverse effects on the dyeing, especially because of the action of these mercaptans on dyestuffs and, in particular, on direct dyestuffs.

Dyeing by means of such compositions also exhibits numerous disadvantages for the hair, the latter being attacked by the mercaptans which must remain in contact with the head of hair for a sufficient length of time to permit the waving thereof.

The combination of a permanent waving and a dyeing treatment of the hair also exhibits disadvantages from the point of view of the frequency of such treatments, because the frequency of the permanent waving treatment must be equal to that of dyeing; as a result, the hair tends to be degraded to a much greater extent, not only because of the large amounts of mercaptan present but also because of the frequency of the application of the compositions in relation to the regrowth of the hair.

The oxidising agent which is used for fixing the perm is generally applied after rinsing and, in such cases, acts for a relatively short time which is generally insufficiently long to develop the dyestuffs which may be present on the hair. Furthermore, due to rinsing, it is impossible, in such a system, to carry out dyeings for lightening the hair since hydrogen peroxide acts only in an acid medium.

These mercaptans are also used as antioxidants in oxidative compositions, for the purpose, in particular, of avoiding changes in the dyeing capacity during manufacture and storage without, however, inhibiting the development of the coloration at the time of application to the hair.

Such compositions were always applied to the head of hair after they had been mixed just before application, with a large excess of oxidising agent with the result that the hair is only in contact with an oxidising composition.

We have now discovered according to the present invention, a hair dyeing process and a composition intended for use in hair dyeing, which make it possible to reduce or overcome the abovementioned disadvantages and combine the action of oxidisable dyestuffs with the action of mercaptans for the purpose of improving the strength of the coloration and uniformity, that is to say of exploiting as far as possible the coloring potential of this type of compound without causing degradation of the hair.

We have also discovered that it is possible to obtain dyeings which lighten the hair to a greater or lesser extent and which moreover possess the abovementioned characteristics.

Furthermore, the process according to the invention makes it possible to dye the hair at a higher temperature than that of the composition applied to the hair, and this leads to an improvement in the strength of the coloration.

It is moreover self-evident that, in addition to the surprising effects resulting from the combination of mercaptans with oxidisable dyestuffs, the use of mercaptans makes it possible to protect the dyeing compositions against accidental oxidation which can take place during manufacture and storage.

The process, according to the present invention, for dyeing keratin fibres, and in particular hair, is essentially characterised in that, in a first stage, a first composition, containing at least one mercaptan present in amounts which do not lead to degradation of the hair, is applied, and in that, in a second stage and without intermediate rinsing, the hair is dyed by developing the oxidisable dyestuffs by means of an oxidising composition.

"Degradation of the hair", as used herein, means that the hair has an unkempt and frizzy appearance and a rough feel, the fibres being damaged in a general way, and this manifests itself, in particular, in a weakening of their mechanical properties.

The amount of mercaptan which makes it possible to avoid such degradation as defined is, in particular, less than 5 g per 100 g of composition.

According to a particularly preferred embodiment of the invention, a first composition, containing at least one mercaptan in the abovementioned concentration and an oxidisable dyestuff, is applied in a first stage and, in a second stage and without intermediate rinsing, an oxidising composition is applied in order to develop the dyestuffs on the hair.

Advantageous results are obtained especially by using amounts of mercaptans which are sufficient to avoid the development of the dyestuffs on the hair during their application in the first stage, and which do not cause degradation of the hair. These amounts are generally more than 1% by weight and less than 5% by weight, and preferably from 1.5 to 3.5% by weight.

The mercaptans which are preferably used according to the invention correspond to the formula:

R—SH    (I)

in which R denotes an alkylene group bonded to a group of formula —COOH, —CONH$_2$, —OH, —SH or —COOR', R' denoting an alkyl group which can, if desired, be substituted by one or more hydroxyl groups, it being possible for the said alkylene group to be substituted by one or more lower alkyl (for example of 1 to 6 carbon atoms), amino or COOH groups, as well as the ammonium, alkali metal and alkaline earth metal salts of these compounds and organic and inorganic acid addition salts thereof.

In formula (I) the alkylene group preferably has 1 to 4 carbon atoms and denotes, in particular, a methylene, ethylene or propylene group; the alkyl group preferably denotes a group having 1 to 6 carbon atoms and, in particular, methyl; the alkali metal or alkaline earth metal salts are preferably sodium salts, potassium salts or calcium salts; the salts of organic or inorganic acids are preferably salts derived from hydrochloric acid, sulphuric acid, acetic acid or tartaric acid.

Preferred compounds of formula (I) are, inter alia, thioglycollic acid, thiolactic acid, β-mercaptopropionic acid, α-monothioglycerol, glycerol thioglycollate, thioglycolamide, cysteine hydrochloride, mercaptosuccinic acid, α,α'-dimercaptoadipic acid, monothiosuccinol and glycol thioglycollate.

These mercaptans can be used by themselves or in a mixture with one another.

Amongst the oxidative dyestuffs, there may be mentioned, more particularly, the oxidative dyestuff precursors of the para type, in particular the compounds corresponding to the formula:

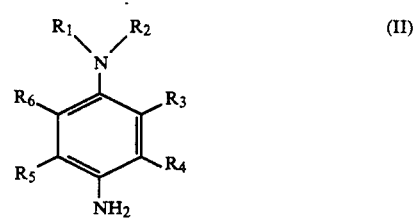

in which R$_1$ and R$_2$ independently of one another denote: hydrogen; a linear or branched alkyl radical which can be chain-terminated by substituents such as: hydroxyl, alkoxy, amino (it being possible for the amino group to be primary, secondary or tertiary or to form part of a ring such as piperidine or morpholino), acylamino, alkyl- or aryl-sulphonylamino, carbalkoxyamino, ureido, carboxyl, carbamoyl in which the nitrogen atom can carry one or two substituents, sulpho and sulphoamido in which the nitrogen atom can carry one or two substituents, it being possible for this alkyl radical to additionally contain, in the chain, one or more hetero-atoms, such as oxygen or nitrogen, and carry other hydroxyl or amino groups; a phenyl radical; or a furfuryl or tetrahydrofurfuryl radical; the radicals R$_1$ and R$_2$ can form, together with the nitrogen atom to which they are attached, a heterocyclic ring such as piperidino or morpholino; and R$_3$, R$_4$, R$_5$ and R$_6$ independently of one another denote: hydrogen; halogen; linear or branched alkyl which is optionally substituted by one or more OH, amino or alkoxy groups; or a group OZ, Z denoting alkyl, hydroxyalkyl, alkoxyalkyl, acylaminoalkyl, carbalkoxyaminoalkyl, methylaminoalkyl, ureidoalkyl, aminoalkyl or mono- or dialkylaminoalkyl, with the proviso that, if R$_2$ denotes the phenyl radical, R$_1$, R$_3$, R$_4$, R$_5$ and R$_6$ denote hydrogen, and that, if R₁ and R₂ are both different from hydrogen, R₃ and R₆ denote hydrogen.

These "para" precursors can be in the form of the free base or of their salts such as the hydrochloride hydrobromide, sulphate, acetate or tartrate.

In the formula of the abovementioned oxidisable dyestuffs, the alkyl groups preferably denote groups having 1 to 6 carbon atoms, such as the methyl, ethyl, propyl, isopropyl, n-butyl and i-butyl groups, alkoxy preferably denotes a group having 1 to 6 carbon atoms, such as methoxy, ethoxy or propoxy, acyl generally denotes a derivative of a carboxylic acid having 1 to 4 carbon atoms, halogen denotes chlorine, bromine and fluorine, and the substituents on the nitrogen atom are preferably alkyl groups having from 1 to 6 carbon atoms.

Amongst the compounds corresponding to the formula II, there may be mentioned: para-phenylenediamine, para-toluylenediamine, methoxy-para-phenylenediamine, chloro-para-phenylenediamine, 2,6-dimethyl-para-phenylenediamine, 2,5-dimethyl-para-phenylenediamine, 2-methyl-5-methoxy-para-phenylenediamine, 2,6-dimethyl-5-methoxy-para-phenylenediamine, N,N-dimethyl-para-phenylenediamine, 3-methyl-4-amino-N,N-diethylaniline, N-mono- and N,N-di-(β-hydroxyethyl)-para-phenylenediamine, 3-methyl-4-amino-N,N-di-(β-hydroxyethyl)-aniline, 3-chloro-4-amino-N,N-di-(β-hydroxyethyl)-aniline, 4-amino-N-ethyl-N-carbamylmethylaniline, 3-methyl-4-amino-N-ethyl-N-carbamylmethylaniline, 4-amino-N-ethyl-N-morpholinoethylaniline, 3-methyl-4-amino-N-ethyl-N-morpholinoethylaniline, 4-amino-N-acetylaminoethylaniline, 4-amino-N-ethyl-N-acetylaminoethylaniline, 3-methyl-4-amino-N-ethyl-N-acetylaminoethylaniline, 4-amino-N-ethyl-N-mesylaminoethylaniline, 3-methyl-4-amino-N-ethyl-N-mesylaminoethylaniline, 4-amino-N-ethyl-N-(β-sulphoethyl)-aniline, 3-methyl-4-amino-N-ethyl-N-(β-sulphoethyl)-aniline, N-(4'-aminophenyl)-morpholine, N-(4'-aminophenyl)-piperidine, 4-amino-N-ethyl-N-piperidinoethylaniline, 3-methyl-4-amino-N-methylaniline, 2-chloro-4-amino-N-ethyl-N-sulphoamidomethylaniline, 2-chloro-4-amino-N-ethylaniline, 2-methyl-4-amino-N-(β-hydroxyethyl)-aniline, 2,5-diaminophenoxyethanol, 4-(β-methoxyethyl)-aminoaniline, N-methyl-para-phenylenediamine, para-aminodiphenylamine, 4-amino-N-(β-hydroxyethyl)-N-(β-mesylaminoethyl)-aniline, 4-amino-N-[β-(β'-hydroxyethoxy)-ethyl]-aniline, 2-N-(β-hydroxyethyl)-amino-5-aminophenoxyethanol, 4-(N-tetrahydrofurfuryl)-aminoaniline and 4-(N-furfuryl)-aminoaniline, 4-amino-N-ethyl-N-(β-hydroxyethyl)aniline.

Other precursors which can be used according to the invention are para-aminophenols, such as para-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol and N-methyl-para-aminophenol, heterocyclic precursors derived from pyridine, such as 2,5-diaminopyridine, 2-dimethylamino-5-aminopyridine, 2-diethylamino-5-aminopyridine or alternatively 2-methyl-6-benzomorpholine and 5-aminoindole, and bis-condensed precursors such as the N,N'-diarylalkylenediamines in which the aryl groups are substituted in the para position by a OH or amino group optionally substituted by an alkyl group and can be substituted on the nucleus by alkyl or halogen, and in which the alkylene group can be interrupted by a hetero-atom, such as O or N, and is optionally substituted by OH or an alkyl group, it being possible for the nitrogen atoms carried by the alkylenediamine group to be substituted by an alkyl, hydroxyalkyl or aminoalkyl group.

Compounds of this type are described, inter alia, in French Pat. No. 2,016,123.

Amongst the compounds of this type, there may be mentioned: N,N'-(4-aminophenyl)-tetramethylenediamine, N,N'-(β-diethylaminoethyl)-N,N'-(4-aminophenyl)-tetramethylenediamine, N-(4-hydroxyphenyl)-N'-(4'-aminophenyl)-ethylenediamine, N,N'-(4-aminophenyl)-N,N'-(β-hydroxyethyl)-tetramethylenediamine and N,N'-(4-aminophenyl)-N,N'-(β-hydroxyethyl)-dimethylenediamine.

The diphenylamines which can be used in the process and the compositions according to the invention are diphenylamines in which the 2 benzene nuclei are substituted in the 4- and 4'-position by 2 groups such as hydroxyl and/or NR'R" in which R' and R" independently or simultaneously denote: hydrogen, alkyl or hydroxyalkyl, and if R" denotes carbamylalkyl, mesylaminoalkyl, acylaminoalkyl, sulphoalkyl, piperidinoalkyl or morpholinoalkyl, R' denotes H or alkyl. The radicals R' and R" can form, together with the nitrogen atom to which they are attached, a piperidino or morpholino heterocyclic ring. The other positions of the 2 benzene nuclei can be occupied by one or more groups such as alkyl or alkoxy in which the alkyl radical can form a heterocyclic ring with a primary or secondary amine group in the 4- or 4'-position, a halogen atom, or a ureido or amino group which is optionally substituted by a hydroxyalkyl, carbamylalkyl, mesylaminoalkyl, acyl or carbalkoxy group.

These diphenylamines can be used in the form of their salts such as the sulphate, hydrobromide, hydrochloride, acetate or tartrate.

These diphenylamines are described in, for example, French Pat. Nos. 1,222,700, 2,056,799, 2,174,473, 2,145,724, 2,262,023, 2,262,024 and 2,261,750 and patent application 75/05,503 of the applicant company, which have been included by way of reference.

The dyestuffs for rapid oxidation are generally polyhydroxybenzenes and polyhydroxynaphthalenes, such as pyrogallol, 1,2,4-trihydroxybenzene, 1,3,5-trihydroxybenzene, 1,4,5-trihydroxynaphthalene and 2,4,5-tri-hydroxytoluene or α-juglone, polyaminobenzenes, such as triaminobenzenes, polyaminophenols, such as di- or tri-aminophenols, polyamino-polyhydroxybenzenes in which the amino groups are optionally substituted by an alkyl radical, and polyhydroxy- and polyhydroxyamino-indoles.

The abovementioned oxidative dyestuff precursors can be combined with couplers or toners, making it possible to develop a coloration on the hair and/or to modify the coloration. As couplers which can be used according to the invention, there may be mentioned monophenol derivatives, meta-diphenols, meta-aminophenols having a free primary, secondary or tertiary amine group or a blocked amine group, and meta-diamines. These various classes can be represented by the general formula:

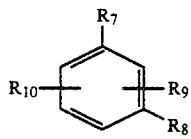
(III)

in which:

when formula (III) represents a phenol coupler, only one of the substituents $R_7$ or $R_8$ denotes OH and the other substituents (R groups), which are different from OH, denote hydrogen, alkyl, alkoxy or halogen, one of the para or ortho positions, relative to the OH group, being free or substituted by halogen or alkoxy;

when formula (III) represents a m-diphenol, $R_7$ and $R_8$ denote OH, it being possible for $R_9$ and $R_{10}$ to denote hydrogen or an alkyl, alkoxy or halogen group;

when formula (III) represents a m-aminophenol, one of the groups $R_7$ or $R_8$ denotes OH and the other group represents

in which:

$R_{11}$ and $R_{12}$, which are identical or different, denote hydrogen, linear or branched alkyl optionally chain-terminated by a OH, alkoxy or optionally mono- or di-substituted amino group, or a heterocyclic ring such as piperidino or morpholino, it being possible for the alkyl group to contain other hydroxy or amino substituents, or chain ether groups in the chain; if one of the substituents $R_{11}$ or $R_{12}$ denotes hydrogen, the other substituent denotes acetyl, carbamyl carbamylalkyl in which the nitrogen atom is optionally mono- or di-substituted, alkyl- or aryl-sulphonyl, sulphonamidoalkyl in which the nitrogen atom is optionally mono- or di-substituted, carbethoxy or mesylaminoalkyl; and $R_9$ and $R_{10}$, which are identical or different, represent hydrogen, halogen, linear or branched alkyl or a group $OZ_1$, $Z_1$ representing alkyl, or alkylene forming with the nitrogen atom of $R_7$ or $R_8$ a morpholino ring; and when formula (III) denotes a m-diamine, $R_7$ and $R_8$ both denote a group

each $R_{13}$ and each $R_{14}$ being the same or different, $R_{13}$ and $R_{14}$, which are identical or different, denoting hydrogen or linear or branched alkyl which is optionally substituted by OH, amino, alkoxy, carbamyl or alkyl- or aryl-sulphonylamino, it being possible for one of the groups $R_{13}$ or $R_{14}$ to denote an alkylsulphonyl, acylamino or carbamylalkyl group if the other denotes hydrogen; and $R_9$ and $R_{10}$, which are identical or different, denote hydrogen, halogen, linear or branched alkyl or $OZ_2$, $Z_2$ denoting alkyl, hydroxyalkyl, alkoxyalkyl, acylaminoalkyl, mesylaminoalkyl, ureidoalkyl or carbalkoxyalkyl, or alkylene forming with the nitrogen atom of $R_7$ or $R_8$ a morpholino ring, and organic or inorganic acid salts thereof such as the hydrochloride, hydrobromide, sulphate or acetate.

In the formulae of the abovementioned couplers, the alkyl groups preferably denote groups having from 1 to 6 carbon atoms, such as methyl, ethyl, propyl, isopropyl, n-butyl and i-butyl groups, alkoxy denotes a group preferably having 1 to 6 carbon atoms, such as methoxy, ethoxy and propoxy, acyl generally denotes a derivative of a carboxylic acid having 1 to 7 carbon atoms, halogen denotes chlorine, bromine and fluorine, and the substituents on the nitrogen atom are preferably alkyl groups having from 1 to 6 carbon atoms.

Amongst the couplers corresponding to the general formula mentioned above, there may be mentioned, more particularly, resorcinols, such as resorcinol, 2-methylresorcinol and 4-chlororesorcinol, meta-aminophenol, 2,4-diaminoanisole, 2-methyl-5-ureidophenol, 2,6-dimethyl-3-aminophenol, 2-methyl-5-acetylaminophenol, 2,6-dimethyl-5-acetylaminophenol, 3-amino-4-methoxyphenol, 2-methyl-5-N-(β-hydroxyethyl)-aminophenol, meta-phenylenediamine, metatoluylenediamine, N-methyl-meta-aminophenol, 6-methyl-3-aminophenol, 2,4-diaminophenoxyethanol, 3-N-diethylaminophenol, 6-methyl-3-N-(β-mesylaminoethyl)-aminophenol, 6-methyl-3-N-carbamylmethylaminophenol, 3-N-carbamylmethylaminophenol and 2-N-(β-hydroxyethyl)-amino-4-aminophenoxyethanol and salts of these compounds.

Other couplers which can be used in the compositions according to the invention include α-naphthol, heterocyclic compounds, and in particular, morpholine derivatives such as 6-hydroxybenzomorpholine and 6-aminobenzomorpholine, pyridine derivatives, such as 2,6-diaminopyridine, pyrazolones and diketone compounds and their salts.

These oxidisable compounds can be used by themselves or in a mixture.

If the composition contains at least one coupler, it is also possible to use oxidative dyestuff precursors of the ortho type, such as ortho-aminophenol or ortho-phenylenediamine which can optionally be substituted on the nitrogen atom or on the benzene nucleus by one or more alkyl, hydroxyalkyl or alkoxy groups.

Results of particular significance can be obtained with the compositions which are defined above and which contain, as oxidative dyestuff precursors of the para type, particularly hindered compounds corresponding to the formula II in which, if $R_1$ and $R_2$ represent hydrogen, at least two of the radicals $R_3, R_4, R_5$ and $R_6$ are different from hydrogen, and a coupler and a mercaptan in the proportions defined above.

The use of these compositions in the method of the present invention is preferred and make it possible, in particular, to overcome the problems, presented by these compounds, of selectivity with respect to the hair.

Amongst the oxidative dyestuff precursors of the para type which give particularly advantageous results in the present invention, there may be mentioned: 2,6-dimethyl-5-methoxy-p-phenylenediamine, 4-(β-methoxyethyl)-aminoaniline, 4-N-(tetrahydrofurfuryl)-aminoaniline, 4-N-(furfuryl)-aminoaniline, 3-methyl-4-amino-N-ethyl-N-mesylaminoethylaniline, 4-amino-N-ethyl-N-carbamylmethylaniline, 3-methyl-4-amino-N-ethyl-N-carbamylmethylaniline, N,N'-(4-aminophenyl)-N,N'-(β-hydroxyethyl)-tetramethylenediamine, N-(4'-aminophenyl)-morpholine, N-(4'-aminophenyl)-piperidine, 4-amino-N-ethyl-N-mesylaminoethylaniline, N,N'-(4-aminophenyl)-N,N'-(β-hydroxyethyl)-dimethylenediamine, 4-amino-N-ethyl-N-piperidinoethylaniline, N,N-di-(β-hydroxyethyl)-para-phenylenediamine sulphate, para-aminodiphenylamine, 4-amino-N-[β-(β'-hydroxyethoxy)-ethyl]-aniline, 2,6-dimethyl-para-phenylenediamine, 4-amino-N-(β-hydroxyethyl)-N-(β-mesylaminoethyl)-aniline and 2-N-(β-hydroxyethyl)-amino-5-aminophenoxyethanol.

These precursors can be used in the form of the free base or of their salts, by themselves or in a mixture, and optionally in the presence of para-phenylenediamines of the formula II.

A further advantageous embodiment of the invention consists of compositions containing at least one diphenylamine chosen from amongst leuco derivatives of indoaniline or of indophenols, such as: 3,5-dimethyl-4-hydroxy-4'-N,N-dimethyl aminodiphenylamine, 2-acetylamino-2',3,5-trimethyl-4-hydroxy-4'-[N-ethyl-N-(β-mesylaminoethyl)]-aminodiphenylamine, 2-acetylamino-2',5-dimethyl-4-hydroxy-4'-(N-ethyl-N-carbamylmethyl)-aminodiphenylamine, 2',3,5,5'-tetramethyl-4-hydroxy-4'-aminodiphenylamine, 2,4-diamino-3-methoxy-4'-hydroxydiphenylamine dihydrochloride, 3,5-dimethyl-4-hydroxy-4'-aminodiphenylamine, 2-(carbamylmethyl)-amino-4-hydroxy-4'-[N,N-di-(β-hydroxyethyl)-amino]-5-methyl-diphenylamine, 3,5-dimethyl-4,4'-dihydroxydiphenylamine, 2'-chloro-3,5-dimethyl-4,4'-dihydroxydiphenylamine hydrochloride, 2,4'-diamino-4-hydroxy-5-methyldiphenylamine, 2-(hydroxyethyl)-amino-5-methyl-4,4'-dihydroxydiphenylamine and 2-amino-5-methyl-4,4'-dihydroxydiphenylamine, and a mercaptan in the abovementioned proportions.

According to a preferred embodiment of the invention, the oxidative dyestuff precursors of the para type are present in an amount from about 0.005% to 10% by weight and preferably from 0.01% to 8% by weight.

The diphenylamines are preferably present in an amount from about 0.005% to 4% by weight. The dyestuffs for rapid oxidation are preferably present in an amount from about 0.01 to 8% by weight. The oxidative couplers are preferably in an amount from about 0.005% to 10% by weight and preferably from 0.01% to 8% by weight.

The pH of the composition applied, according to the invention, in the first stage is generally from 7 to 12 and preferably from 8.5 to 11. It can be adjusted with the aid of cosmetically acceptable alkalising agents such as ammonia, alkylamines, alkanolamines, such as mono- di- or tri-ethanolamine, alkylalkanolamines, such as aminomethyl propanol or aminomethylpropanediol, sodium hydroxide or potassium hydroxide, or sodium carbonate or potassium carbonate or mixtures thereof.

In addition, this composition can be buffered to a given pH with the aid of organic or inorganic salts such as neutral or acid phosphates or carbonates of ammonium, an alkali metal or an alkaline earth metal.

The oxidising composition applied in the second stage contains a cosmetically acceptable oxidising agent, such as hydrogen peroxide, suitably at a concentration from 0.1 to 12% by weight, urea peroxide or a persalt such as ammonium persulphate, sodium persulphate or potassium persulphate. The pH of this composition should be adjusted so as to give optimum development of the coloration obtained after penetration, into the fibre, of this composition and of the composition applied in the first stage.

These compositions can also contain direct dyestuffs; they can be present in the said first composition, if they are stable in the latter, or in the second composition, if they are stable in an oxidising medium. Thus, the process according to the invention not only makes it possible to utilise the colouring potential of the various oxidisable dyestuffs to the maximum extent, but it also makes it possible to combine the action of these dyestuffs with that of direct dyestuffs which previously could not be used under the normal conditions of use of oxidative dyes.

The direct dyestuffs are preferably present in an amount from about 0.005% to 3% by weight.

The direct dyestuffs which can more particularly be used according to the invention are anthraquinone dyestuffs, 1,4-hydroxynaphthaquinones, such as lawsone, nitrobenzene derivatives, nitrated diphenylamines, such as: nitrophenylenediamines, nitroaminophenols, dinitroaminophenols, dinitroaminobenzenes, nitroaminobenzenes or the nitrodiphenylamines described, in particular, in French Pat. No. 2,211,210 which is hereby incorporated by reference, 1-hydroxy-2-amino-4,6-dinitrobenzene, 2-nitro-p-phenylenediamine, 1-amino-2-nitro-4-N-methylaminobenzene, 1-hydroxy-2-amino-5-nitrobenzene, 4-nitro-m-phenylenediamine, 1-methoxy-3-nitro-4-N-(β-hydroxyethyl)-aminobenzene, 1-(β-hydroxyethoxy)-3-nitro-4-aminobenzene, 2-N-(β-hydroxyethyl)-amino-5-nitroanisole, 1-amino-2-nitro-4-N-(β-hydroxyethyl)-aminobenzene, 1-N-methylamino-2-nitro-4-N,N-bis-(β-hydroxyethyl)-aminobenzene, 1-(N-methylamino)-2-nitro-4-[N-methyl-N-(β-hydroxyethyl)-amino]-benzene, 3-nitro-4-N-(β-hydroxyethyl)-aminophenol, 2,6-dimethyl-3-nitro-4-N-(β-hydroxyethyl)-aminophenol, 4-nitro-o-phenylenediamine, 2-amino-4-nitrophenol, 2-nitro-4-aminophenol, 1,4-[bis-N-(β-hydroxyethyl)-amino]-2-nitrobenzene, 1-amino-2-N-(β-hydroxyethyl)-amino-5-nitrobenzene, 4-N'-(β-hydroxyethyl)-amino-N,N-(β-hydroxyethyl)-aniline, 2-N-(β-hydroxyethyl)-amino-5-nitrophenoxyethanol, 1-amino-2-[tris-(hydroxymethyl)-methyl]-amino-5-nitrobenzene, 1-N-(β-hydroxyethyl)-amino-2-nitrobenzene, 2-nitro-4'-bis (β-hydroxyethyl)-aminodiphenylamine, 3-nitro-4-N'-(β-hydroxyethyl)-amino-N,N-(β-hydroxyethyl)-aniline, 2-nitro-4'-hydroxydiphenylamine, 2-nitro-4-aminodiphenylamine, 1-amino-3-nitro-4-N-(β-hydroxyethyl)-aminobenzene, 2-N,N-bis-(β-hydroxyethyl)-amino-5-nitrophenol, 1-amino-2-nitro-4-N-(β-hydroxyethyl)-amino-5-chlorobenzene, 3-nitro-b 4-aminophenol, 5-amino-2-nitrophenol, 3-nitro-4-N'-(β-hydroxyethyl)-amino-N-methyl-N-(β-hydroxyethyl)-aniline and 3-nitro-4-N'-(β-hydroxyethyl)-amino-N-methylaniline.

The duration of application of the first composition is generally 5 to 45 minutes, and preferably 5 to 20 minutes, whereas the duration of application of the oxidising composition is generally 5 to 45 minutes and preferably 10 to 40 minutes.

During this process, it is possible to dye the hair in a fairly light colour by varying the application time and the amount of oxidising agent. It is also possible to vary the strength of the coloration by varying the amount of mercaptan (within the specified range).

According to this variant of the present invention, it is also possible to add all or part of the mercaptan, just before use, in the abovementioned amounts, to the composition containing the oxidisable dyestuff.

The other embodiment of this process consists in applying, in a first stage, the first composition containing the mercaptan in the proportions defined above and, in a second stage and without intermediate rinsing, a second composition containing the oxidising agent and also the oxidisable dyestuffs for dyeing the hair.

The composition intended for use in the process for dyeing keratin fibres, and in particular human hair, which constitutes a further aspect of the present invention, is characterised in that it contains at least one oxidisable dyestuff and at least one mercaptan in an amount which is sufficient to inhibit the development of the coloration of the fibres during the application, but insufficient to cause degradation of the fibres. The amount of mercaptan is preferably more than 1% and less than 5% by weight; particularly significant results can be obtained for amounts from 1.5 to 3.5% by weight.

A particularly advantageous embodiment, which constitutes a preferred method of carrying out the invention, involves the use of such a composition which contains at least one particularly hindered base, defined above, at least one coupler and at least one mercaptan in the proportions mentioned above. This composition can be used in the first stage of the process of this invention.

The compositions containing at least one oxidisable dyestuff and the mercaptan, and also the oxidising compositions according to the invention, can be in the form of, for example, aqueous, thickened, gelled or gellable compositions or creams, which compositions can be packaged in an aerosol.

The gelled or gellable compositions can be obtained either from polyoxyethylenated or polyglycerolated nonionic compounds in the presence of solvents, or from soaps of liquid fatty acids, such as oleic acid or isostearic acid, in the presence of solvents in an aqueous vehicle.

The fatty acids are generally used to form the soaps at concentrations from 0.5 to 15% by weight.

The alkalising agents used to form the soaps are suitably sodium hydroxide, potassium hydroxide, ammonia, monoethanolamine, diethanolamine or triethanolamine or mixtures thereof.

Amongst the polyoxyethylenated non-ionic compounds, there may be mentioned, in particular, oxyethyleneated nonyl phenol containing 4 mols of ethylene oxide (per mole of phenol) and oxyethyleneated nonylphenol containing 9 mols of ethylene oxide.

These constituents are preferably present at concentrations from 5 to 60% by weight.

Amongst the polyglycerolated non-ionic compounds, there may be mentioned, in particular, glycerolated oleyl alcohol containing 2 mols of glycerol and glycerolated oleyl alcohol containing 4 mols of glycerol.

These constituents are preferably present at concentrations from 5 to 60% by weight.

Amongst the solvents which can be used, there may be mentioned ethyl, butyl, isopropyl and benzyl alcohols, and glycols or glycol ethers, such as methylcellosolve, ethylcellosolve, butylcellosolve(ethylene glycol monomethyl, monoethyl and monobutyl ether)propylene glycol, carbitol and butyl carbitol and also mixture thereof.

These constituents are preferably present at concentrations from 2 to 40% by weight.

All the specified concentrations are based on the total weight of the dyeing composition.

If the compositions are in the form of creams, their formulation is essentially based on soaps or fatty alcohols in the presence of emulsifying agents and in an aqueous vehicle.

The soaps can be formed from natural or synthetic fatty acids having from 12 to 18 carbon atoms, such as lauric acid, myristic acid, palmitic acid and stearic acid, and from alkalising agents such as sodium hydroxide, potassium hydroxide, ammonia, monoethanolamine, diethanolamine and triethanolamine. The fatty acids are preferably present in the creams of the invention at concentrations from 10 to 30% by weight.

The creams can also be formulated from natural or synthetic fatty alcohols having between 12 and 18 carbon atoms, in a mixture with emulsifying agents. Amongst these fatty alcohols, there may be mentioned, in particular, lauryl alcohol, alcohols derived from copra fatty acids, myristyl alcohol, cetyl alcohol, stearyl alcohol and hydroxystearyl alcohol. The concentrations of fatty alcohols in the creams of the invention is generally 5 to 25% by weight.

The emulsifying agents which can be used in the compositions according to the present invention include polyoxyethyleneated or polyglycerolated fatty alcohols such as, polyoxyethylenated oleyl alcohol containing from 10 to 30 mols of ethylene oxide, polyoxyethyleneated cetyl alcohol containing from 6 to 10 mols of ethylene oxide, polyoxyethyleneated lauryl alcohol containing 12 mols of ethylene oxide, oxyethyleneated cetyl/stearyl alcohol containing 10 or 15 mols of ethylene oxide, polyoxyethyleneated oleyl/cetyl alcohol containing 30 mols of ethylene oxide, polyoxyethyleneated stearyl alcohol containing 10, 15 or 20 mols of ethylene oxide, polyglycerolated oleyl alcohol containing 4 mols of glycerol and synthetic fatty alcohols which contain from 9 to 15 carbon atoms and are polyoxyethyleneated with 5 or 10 mols of ethylene oxide; polyoxyethyleneated castor oil can also be used. These non-ionic emulsifying agents are present in the compositions of the invention in an amount of 1 to 25% by weight.

Other emulsifying agents which can be used according to the invention include alkyl-sulphates which may or may not be oxyethyleneated, such as sodium lauryl-sulphate, ammonium lauryl-sulphate, sodium cetyl-/stearyl-sulphate, triethanolamine cetyl-/stearyl-sulphate, monoethanolamine lauryl-sulphate or triethanolamine lauryl-sulphate, the sodium salt of the sulphate half-ester of oxyethyleneated lauryl alcohol containing, for example, 2.2 mols of ethylene oxide, and the monoethanolamine salt of the sulphate half-ester of oxyethyleneated lauryl alcohol containing, for example, 2.2 mols of ethylene oxide.

These constituents are preferably present in these compositions at a concentration from 1 to 15% by weight.

In addition to the soaps, fatty alcohols and emulsifying agents, the creams according to the invention can contain adjuvants, such as fatty amides, which are usually employed in compositions of this kind.

Fatty amides which are preferably used are mono- or di-ethanolamides of acids derived from copra, of lauric acid or of oleic acid; they are generally used at a concentration up to 10% by weight, relative to the total weight of the composition.

It can be advantageous to add, to the mercaptan used according to the invention, an antioxidant which is intended to avoid changes in the dyeing capacity. Examples which may be mentioned are sodium sulphite, sodium bisulphite and sodium dithionite, ascorbic acid and isoascorbic acid and their esters or their salts, homogentisic acid, 1-phenyl-3-methylpyrazol-5-one and hydroquinone. The concentrations of these compounds is generally up to 1%.

The compositions according to the invention can also contain solvents, thickeners, treating agents, sequestering agents, such as ethylenediaminetetraacetic acid, diethylenetriaminepentaacetic acid or their salts, perfumes, preservatives and sun filters, for example.

Solvents can be added to the composition in order to solubilise the dyestuffs which are insufficiently soluble in water. In this case, the solvents which can be used may be the same as those indicated above for the composition of the gellable liquids.

Amongst the thickeners which can be used according to the invention, there may be mentioned sodium alginate, gum arabic, cellulose derivatives, such as methylcellulose, hydroxyethylcellulose, hydroxypropylcellulose, hydroxypropylmethylcellulose and carboxymethylcellulose, or carboxyvinylic polymers such as the "Carbopols".

These constituents are typically present in an amount from 0.5 to 5%.

The treating agents which can be used according to the invention are mainly intended to improve the feel of the hair and to make the hair easier to comb out. For example, they can be quaternary amines, such as trimethylcetylammonium bromide, cetylpyridinium chloride, stearyltrimethylammonium chloride, dilauryldimethylammonium chloride or distearyldimethylammonium chloride, used by themselves or in a mixture, or cationic polymers, such as quaternary derivatives of cellulose ether, for example JR 400 of Messrs. Union Carbide, polydiallyldimethylammonium chlorides, such as Merquat 550 and Merquat 100 of Messrs. Merck, quaternised polymers, such as those defined in French Pat. Nos. 2,270,846, 2,316,271, 2,189,434 and 75/15,161, or the crosslinked, graft cationic copolymers described in French Pat. No. 73/22,222 of the applicant company, used by themselves or in a mixture.

The concentration of treating agent is generally from 0.1 to 5% by weight.

The two-stage process according to the invention also makes it possible to vary the consistency and the form of the dyeing carrier between the time of application of the compositions to the hair and the dyeing itself. It is thus possible, in an advantageous embodiment of the invention, to apply the first composition to the hair, in the form of a liquid, thus improving the impregnation of the hair, the second composition containing ingredients which act on the first composition on the hair, modifying its consistency, for example by gelling, which improves the retention of the composition on the hair.

The following Examples further illustrate the present invention.

In the following Examples:
Remcopal 334 denotes oxyethyleneated nonylphenol containing 4 mols of ethylene oxide (per mol of phenol), sold under the name Remcopal 334 by Messrs. GERLAND Remcopal 349 denotes oxyethyleneated nonylphenol containing 9 mols of ethylene oxide, sold under the name Remcopal 349 by Messrs. GERLAND.

Masquol DTPA denotes the pentasodium salt of diethylenetriaminepentaacetic acid, sold by Messrs. PROTEX.

Polychol 5 denotes oxyethyleneated lanoline fatty alcohol containing 5 mols of ethylene oxide, sold under the name Polychol 5 by Messrs. CRODA Ltd.

Polychol 20 denotes oxyethyleneated lanoline fatty alcohol containing 20 mols of ethylene oxide, sold under the name Polychol 20 by Messrs. CRODA Ltd.

Alfol C 16/18 E denotes the cetyl/stearyl alcohol sold under the name Alfol C 16/18 E by Messrs. CONDEA.

Lanette wax E denotes the C16-C18 sodium cetyl-/stearyl-sulphate sold under the name Lanette Wax E by Messrs. HENKEL.

Cemulsol B denotes the oxyethyleneated castor oil sold under the name Cemulsol B by Messrs. RHONE POULENC.

Amphoteric compound I denotes the compound:

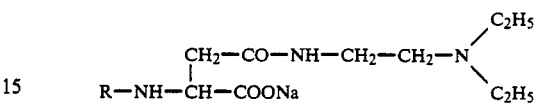

in which R represents the alkyl radicals derived from the acids of copra.

Carbopol 934 denotes the crosslinked polyacrylic acid sold under the name Carbopol 934 by Messrs. Goodrich Chemicals. Comperlan KD denotes diethanolamides derived from copra fatty acids.

EXAMPLE NO. 1

The following dyeing composition is prepared:

| Part $P_1$: | |
|---|---|
| 4-($\beta$-Methoxyethyl)-aminoaniline dihydrochloride | 1.2 g |
| 2-Methyl-5-N—($\beta$-hydroxyethyl)-aminophenol | 0.85 g |
| Remcopal 334 | 21 g |
| Remcopal 349 | 24 g |
| Oleic acid | 4 g |
| Trimethylcetylammonium bromide | 3 g |
| Butylglycol | 3 g |
| Absolute ethyl alcohol | 14 g |
| Masquol DTPA | 2.5 g |
| Sodium bisulphite | 0.5 g |
| Hydroquinone | 0.2 g |
| 1-Phenyl-3-methylpyrazol-5-one | 0.2 g |
| Sodium bicarbonate | 0.35 g |
| Sodium hydroxide | 0.07 g |
| Monoethanolamine | 4.5 g |
| Thioglycollic acid | 1.5 g |
| Water q.s.p. | 100 g |
| The thioglycollic acid is added at the time of use. | |
| Part $P_2$: | |
| Polychol 5 | 3.3 g |
| Polychol 20 | 1.7 g |
| Stearyl alcohol | 5 g |
| Hydrogen peroxide of 100 volumes strength | 20 g |
| Phosphoric acid q.s.p. | pH 3 |
| Water q.s.p. | 100 g |

14 g of the part $P_1$ of the composition are applied for 10 minutes to two swatches of grey hair, one of which has undergone a curling treatment by means of a perming liquid.

14 g of the part $P_2$ are then added, whilst massaging these swatches thoroughly.

After a further 20 minutes, the two swatches are rinsed with warm water, shampooed and rinsed.

The shade and the strength of coloration of these two swatches are approximately the same.

EXAMPLE NO. 2

The composition and the process are identical to those of Example 1, except that the percentage of thioglycollic acid introduced into the part $P_1$ at the time of use has been increased from 1.5 to 3 g % and the amount of monoethanolamine has been increased from 4.5 to 5.5 g %.

The uniformity of the resulting shade is perfect but this is not the case if this dyeing composition is applied in accordance with the usual method, that is to say mixing the same amount of the parts $P_1$ and $P_2$ before application.

EXAMPLE NO. 3

The following dyeing composition is prepared:

| Part $P_3$: | |
|---|---|
| N,N—di-(β-hydroxyethyl)-para-phenylenediamine sulphate monohydrate | 2 g |
| Para-aminophenol | 0.5 g |
| Resorcinol | 0.3 g |
| Meta-aminophenol | 1 g |
| 2-Methyl-5-N—(β-hydroxyethyl)-aminophenol | 1.1 g |
| Alfol C 16/18 E | 8 g |
| Lanette wax E | 0.5 g |
| Cemulsol B | 1 g |
| Oleyl diethanolamide | 1.5 g |
| Cysteine hydrochloride | 0.1 g |
| Ammonium thioglycollate | 1.2 g |
| α,α'-Dimercaptoadipic acid | 0.7 g |
| Sodium bicarbonate | 0.35 g |
| Sodium hydroxide | 0.07 g |
| 22° Be strength ammonia solution | 11 cc |
| Ethylenediaminetetraacetic acid | 0.3 g |
| Water q.s.p. | 100 g |
| Part $P_4$: | |
| Polychol 5 | 3.3 g |
| Polychol 20 | 1.7 g |
| Stearyl alcohol | 5 g |
| Hydrogen peroxide of 100 volumes strength | 30 g |
| Phosphoric acid q.s.p. | pH 3 |
| Water q.s.p. | 100 g |

The procedure followed is exactly as for Example 1.

After a treatment time of 30 minutes, shampooing and drying, the two swatches are uniformly coloured light chestnut, regardless of their degree of sensitisation.

On the other hand, swatches of white hair which has been treated with the same oxidative compositions, but to which these compositions have been applied for 30 minutes in accordance with the usual method, are coloured:

blond, in the case of the swatches of natural grey hair, and light chestnut, in the case of the swatches of grey hair which had been permed beforehand.

EXAMPLE NO. 4

The following dyeing composition is prepared:

| Part $P_5$: | |
|---|---|
| 4-Amino-N—ethyl-N—mesylaminoethylaniline dihydrochloride | 3.7 g |
| Para-aminophenol | 0.22 g |
| Resorcinol | 0.13 g |
| Meta-aminophenol | 0.43 g |
| 2-Methyl-5-N—(β-hydroxyethyl)-aminophenol | 0.22 g |
| Cetyl alcohol | 12 g |
| 20% strength ammonium lauryl-sulphate solution | 8 g |
| Cetyl/stearyl alcohol containing 15 mols of ethylene oxide | 2 g |
| Lauryl alcohol | 4 g |
| Masquol DTPA | 2 g |
| Ammonium thiolactate | 1.5 g |
| Sodium bicarbonate | 0.4 g |
| Sodium hydroxide | 0.1 g |
| 22° Be strength ammonia solution | 14 cc |
| Water q.s.p. | 100 g |
| Part $P_6$: | |
| Polychol 5 | 3.3 g |
| Polychol 20 | 1.7 g |
| Stearyl alcohol | 5 g |
| Hydrogen peroxide of 100 volumes strength | 40 g |
| Phosphoric acid q.s.p. | pH 3 |
| Water q.s.p. | 100 g |

40 g of the part $P_5$ are applied to a head of hair which has been dyed light chestnut and has been partially sensitised by previous hair treatments.

After 10 minutes, 20 g of the part $P_6$ are added thereto, without rinsing and whilst carefully massaging the head of hair, and the whole is left for a further 20 minutes. After rinsing, shampooing and drying, the hair is uniformly coloured dull chestnut.

EXAMPLE NO. 5

The following dyeing composition is prepared:

| Part $P_7$: | |
|---|---|
| Remcopal 334 | 21 g |
| Remcopal 349 | 24 g |
| Oleic acid | 4 g |
| Trimethylcetylammonium bromide | 3 g |
| Butylglycol | 3 g |
| Absolute ethyl alcohol | 14 g |
| Ethylenediaminetetraacetic acid | 0.2 g |
| Thiolactic acid | 2 g |
| Sodium bicarbonate | 0.35 g |
| Sodium hydroxide | 0.07 g |
| 22° Be strength ammonia solution | 11 cc |
| Water q.s.p. | 100 g |
| Part $P_8$: | |
| 2,6-Dimethyl-5-methoxy-para-phenylenediamine dihydrochloride | 3 g |
| Para-aminophenol | 0.7 g |
| 6-Aminobenzomorpholine dihydrochloride | 0.5 g |
| Resorcinol | 0.5 g |
| Meta-aminophenol | 0.3 g |
| 2-Methyl-5-N—(β-hydroxyethyl)-aminophenol | 0.3 g |
| Cetyl alcohol | 12 g |
| 20% strength ammonium lauryl-sulphate solution | 8 g |
| Cetyl/stearyl alcohol containing 15 mols of ethylene oxide | 2 g |
| Lauryl alcohol | 4 g |
| Ethylenediaminetetraacetic acid | 0.2 g |
| Sodium bisulphite | 1.5 g |
| 22° Be strength ammonia solution | 11 cc |
| Water q.s.p. | 100 g |

20 g of the part $P_7$ are applied for 5 minutes to the roots of a head of hair which has been dyed blond one month previously.

The product is then spread over the whole of the head of hair, and a cream obtained by mixing 40 g of the part $P_8$ with 20 g of a solution $P_9$ having the following composition:

| Part $P_9$: | |
|---|---|
| Polychol 5 | 3.3 g |
| Polychol 20 | 1.7 g |
| Stearyl alcohol | 5 g |
| Hydrogen peroxide of 100 volumes strength | 40 g |
| Phosphoric acid q.s.p. | pH 3 |
| Water q.s.p. | 100 g | is added.

The head of hair is massaged for 20 minutes and then rinsed and shampooed.

After drying, an attractive, uniform chestnut tint is obtained.

EXAMPLE NO. 6

The following dyeing composition is prepared:

| Part P$_{10}$: | |
|---|---|
| 2,6-Dimethyl-5-methoxy-para-phenylenediamine dihydrochloride | 4.5 g |
| Para-aminophenol | 1 g |
| 6-Aminobenzomorpholine dihydrochloride | 1 g |
| Resorcinol | 0.6 g |
| Meta-aminophenol | 0.6 g |
| 2-Methyl-5-N—($\beta$-hydroxyethyl)-aminophenol | 1.7 g |
| Alfol C 16/18 E | 8 g |
| Lanette wax E | 0.5 g |
| Cemulsol B | 1 g |
| Oleyl diethanolamide | 1.5 g |
| Masquol DTPA | 2.5 g |
| Thioglycollic acid | 1 g |
| Mercaptosuccinic acid | 0.8 g |
| Sodium bicarbonate | 0.4 g |
| Sodium hydroxide | 0.1 g |
| 22° Be strength ammonia solution | 12 cc |
| Water q.s.p. | 100 g |

30 g of the part P$_{10}$ are applied for 10 minutes to the roots of a grey head of hair which has been permanently waved 4 months earlier.

The product is then spread over the whole of the head of hair, and 30 g of the part P$_2$ (identical to that of Example 1) are incorporated gradually.

This mixture is left in contact with the head of hair for 20 minutes.

After rinsing, shampooing and drying, the hair is uniformly colored brown, whereas, under usual conditions of application, the same composition colours the roots light chestnut and the permed parts black.

EXAMPLE NO. 7

The following dyeing composition is prepared:

| Part P$_{11}$: | |
|---|---|
| Para-phenylenediamine | 0.95 g |
| 4-Amino-N—ethyl-N—mesylaminoethylaniline dihydrochloride | 0.3 g |
| Resorcinol | 0.05 g |
| 2,4-Diaminophenoxyethanol dihydrochloride | 0.41 g |
| Remcopal 334 | 3 g |
| Remcopal 349 | 2.5 g |
| Oleic acid | 5 g |
| Trimethylcetylammonium bromide | 2 g |
| Amphoteric compound I | 2 g |
| Oleyl alcohol | 5 g |
| Copra diethanolamide | 7 g |
| Butylglycol | 3 g |
| Absolute ethyl alcohol | 5.5 g |
| Propylene glycol | 3 g |
| Ethylenediaminetetraacetic acid | 0.5 g |
| Cysteine hydrochloride | 0.1 g |
| Thioglycollic acid | 0.7 g |
| $\alpha,\alpha'$-Dimercaptoadipic acid | 0.7 g |
| Hydroquinone | 0.2 g |
| Sodium bicarbonate | 0.4 g |
| Sodium hydroxide | 0.1 g |
| 22° Be strength ammonia solution | 12 cc |
| Water q.s.p. | 100 g |

50 g of the part P$_{11}$ are applied for 10 minutes to a natural chestnut head of hair containing a high percentage of white hair. 25 g of the part P$_6$ (identical to that of Example 4) are then added, without rinsing.

After 20 minutes, the head of hair is rinsed, shampooed and dried; it is coloured a perfectly uniform black-blue.

EXAMPLE NO. 8

The following dyeing composition is prepared:

| Part P$_{12}$: | |
|---|---|
| N,N—Di-($\beta$-hydroxyethyl)-para-phenylenediamine | 5.4 g |
| Para-aminophenol | 0.5 g |
| Resorcinol | 0.3 g |
| Meta-aminophenol | 1 g |
| 2-Methyl-5-N—($\beta$-hydroxyethyl)-aminophenol | 0.5 g |
| Remcopal 334 | 21 g |
| Remcopal 349 | 24 g |
| Oleic acid | 4 g |
| Trimethylcetylammonium bromide | 3 g |
| Carbopol 934 | 0.5 g |
| Butylglycol | 3 g |
| Absolute ethyl alcohol | 14 g |
| Ethylenediaminetetraacetic acid | 0.2 g |
| Mercaptosuccinic acid | 1.5 g |
| Thiolactic acid | 1.5 g |
| Hydroquinone | 0.2 g |
| 1-Phenyl-3-methylpyrazol-5-one | 0.2 g |
| Sodium bicarbonate | 0.35 g |
| Sodium hydroxide | 0.07 g |
| 22° Be strength ammonia solution | 13 cc |
| Water q.s.p. | 100 g |

The thiolactic acid is introduced at the time of use. 30 g of the part P$_{12}$ are applied to the non-permed roots of a natural chestnut head of hair containing a high percentage of white hair.

After 5 minutes, a further 10 g of the part P$_{12}$ are added and the total amount is spread over the whole of the head of hair.

After 3 minutes, 40 g of the part P$_4$ are incorporated gradually, whilst massaging the head of hair thoroughly. The mixture is left for about 20 minutes before shampooing and rinsing the head of hair which is uniformly coloured black-blue.

EXAMPLE NO. 9

The following dyeing composition is prepared:

| Part P$_{13}$: | |
|---|---|
| 2,6-Dimethyl-5-methoxy-para-phenylenediamine dihydrochloride | 1.5 g |
| Para-aminophenol | 0.7 g |
| 6-Aminobenzomorpholine dihydrochloride | 0.07 g |
| Resorcinol | 0.5 g |
| 2-Methyl-5-N—($\beta$-hydroxyethyl)-aminophenol | 0.9 g |
| Remcopal 334 | 3 g |
| Remcopal 349 | 2.5 g |
| Oleic acid | 5 g |
| Trimethylcetylammonium bromide | 2 g |
| Amphoteric compound I | 2 g |
| Oleyl alcohol | 5 g |
| Copra diethanolamide | 7 g |
| Butylglycol | 3 g |
| Absolute ethyl alcohol | 5.5 g |
| Propylene glycol | 3 g |
| Masquol DTPA | 2.5 g |
| Cysteine hydrochloride | 0.25 g |
| Ammonium thiolactate | 1.25 g |
| Sodium bisulphite solution | 1 cc |
| Hydroquinone | 0.2 g |
| Sodium bicarbonate | 0.4 g |
| Sodium hydroxide | 0.1 g |
| 22° Be strength ammonia solution | 11 cc |
| Water q.s.p. | 100 g |

The mercaptans can be introduced at the time of use. 40 g of the part P$_{13}$ are applied for 10 minutes to a head of hair which has been dyed light blond.

20 g of the part $P_6$ are then added, without rinsing, and, after 30 minutes, the head of hair is rinsed, shampooed and dried; it is coloured golden coppery deep blond.

EXAMPLE NO. 10

The following dyeing composition is prepared:

| Part $P_{14}$: | |
|---|---|
| Para-phenylenediamine | 0.45 g |
| Alfol C 16/18 E | 8 g |
| Lanette Wax E | 0.5 g |
| Cemulsol B | 1 g |
| Oleyl diethanolamide | 1.5 g |
| Masquol DTPA | 2.5 g |
| Thiolactic acid | 2 g |
| 22° Be strength ammonia solution | 11 cc |
| Water q.s.p. | 100 g |

40 g of the part $P_{14}$ are applied for 15 minutes to a head of hair which has been dyed blond, 40 g of the part $P_4$ are then added, without rinsing, and the mixture is left on the head of hair for a further 20 minutes.

After rinsing, shampooing and drying, the hair is uniformly coloured very deep chestnut.

EXAMPLE NO. 11

The following dyeing composition is prepared:

| Part $P_{15}$: | |
|---|---|
| Alfol C 16/18 E | 8 g |
| Lanette wax E | 0.5 g |
| Cemulsol B | 1 g |
| Oleyl diethanolamide | 1.5 g |
| Masquol DTPA | 2.5 g |
| Thioglycollic acid | 1 g |
| Mercaptosuccinic acid | 0.5 g |
| Sodium bicarbonate | 0.4 g |
| Sodium hydroxide | 0.1 g |
| 22° Be strength ammonia solution | 10 cc |
| Water q.s.p. | 100 g |
| Part $P_{16}$: | |
| 2,6-Dimethyl-5-methoxy-para-phenylenediamine dihydrochloride | 4.5 g |
| Para-aminophenol | 1 g |
| 6-Aminobenzomorpholine dihydrochloride | 1 g |
| Resorcinol | 0.6 g |
| Meta-aminophenol | 0.6 g |
| 2-Methyl-5-N—(β-hydroxyethyl)-aminophenol | 1.7 g |
| Remcopal 334 | 22 g |
| Remcopal 349 | 22 g |
| Butylglycol | 8 g |
| Propylene glycol | 8 g |
| Masquol DTPA | 2.5 g |
| Hydroquinone | 0.2 g |
| Ammonium thiolactate | 0.5 g |
| 22° Be strength ammonia solution | 11 cc |
| Water q.s.p. | 100 g |

25 g of the part $P_{15}$ are applied to the roots of a light chestnut head of hair which has been permed 3 months previously.

After 10 minutes, the product is spread over the whole of the head of hair and, after a few minutes, 80 g of the gel obtained by mixing equal weights of the part $P_{16}$ and a 9% strength solution of hydrogen peroxide are applied to the whole head of hair.

30 minutes after the start of the application, the head of hair is rinsed, shampooed and dried; it has a chestnut shade of good uniformity.

EXAMPLE NO. 12

The following dyeing composition is prepared:

| Part $P_{17}$: | |
|---|---|
| Para-toluylenediamine | 1.10 g |
| 4-Amino-N—(β-hydroxyethyl)-N—mesylaminoethyl-aniline dihydrochloride | 0.2 g |
| Resorcinol | 0.05 g |
| 2-N—(β-hydroxyethyl)-amino-4-aminophenoxyethanol dihydrochloride | 0.5 g |
| Remcopal 334 | 21 g |
| Remcopal 349 | 24 g |
| Oleic acid | 4 g |
| Trimethylcetylammonium bromide | 3 g |
| Butylglycol | 3 g |
| Absolute ethyl alcohol | 14 g |
| Masquol DTPA | 2.5 g |
| Cysteine hydrochloride | 0.1 g |
| Mercaptosuccinic acid | 0.3 g |
| Thioglycerol | 1.2 g |
| Hydroquinone | 0.1 g |
| Sodium bicarbonate | 0.4 g |
| Sodium hydroxide | 0.1 g |
| 22° Be strength ammonia solution | 11 cc |
| Water q.s.p. | 100 g |

40 g of the part $P_{17}$ are applied to a head of hair which has been coloured chestnut, and 40 g of the part $P_4$ are added after 10 minutes.

The whole is left on the head of hair for 20 minutes and the hair is then rinsed carefully and dried; in this way, it is uniformly coloured brown.

EXAMPLE NO. 13

The following dyeing composition is prepared:

| Part $P_{18}$: | |
|---|---|
| 4-(β-Methoxyethyl)-aminoaniline dihydrochloride | 2.4 g |
| 4-Amino-N—ethyl-N—carbamylmethylaniline | 0.6 g |
| Cetyl alcohol | 12 g |
| 20% strength ammonium lauryl-sulphate solution | 8 g |
| Cetyl/stearyl alcohol containing 15 mols of ethylene oxide | 2 g |
| Lauryl alcohol | 4 g |
| Ethylenediaminetetraacetic acid | 0.2 g |
| Thioglycollic acid | 1.7 g |
| 22° Be strength ammonia solution | 12 cm$^3$ |
| Water q.s.p. | 100 g |

40 g of the part $P_{18}$ are applied to a head of hair containing 100% of white hair. After 10 minutes, 20 g of the part $P_6$ are added thereto, without rinsing and whilst massaging the head of hair.

After a further 20 minutes, and after rinsing and drying, the hair is uniformly coloured brown.

EXAMPLE NO. 14

The following dyeing composition is prepared:

| Part $P_{19}$: | |
|---|---|
| 1,2,4-Trihydroxybenzene | 1.3 g |
| Hydroxyethylcellulose sold under the name Cellosize WP 4400 by Messrs. Carbide and Carbon | 2 g |
| Ethylenediaminetetraacetic acid | 0.2 g |
| Thioglycollic acid | 2 g |
| 22° Be strength ammonia solution q.s.p. | pH 9.5 |
| Water q.s.p. | 100 g |

The powdered 1,2,4-trihydroxybenzene is introduced at the time of use. 40 g of the part $P_{19}$ are applied for 15 minutes to an entirely grey head of hair and 40 g of the part P$_2$ are then added, without rinsing.

30 minutes after the start of the application, the hair is rinsed and dried and is uniformly coloured very natural dull chestnut.

EXAMPLE NO. 15

The following dyeing composition is prepared:

| Part P$_{20}$: | |
|---|---|
| N—Methyl-para-phenylenediamine | 1 g |
| 2,6-Dimethyl-para-phenylenediamine | 0.3 g |
| Remcopal 334 | 3 g |
| Remcopal 349 | 2.5 g |
| Oleic acid | 5 g |
| Trimethylcetylammonium bromide | 2 g |
| Amphoteric compound I | 2 g |
| Oleyl alcohol | 5 g |
| Comperlan KD | 7 g |
| Butylglycol | 3 g |
| Absolute ethyl alcohol | 5.5 g |
| Propylene glycol | 3 g |
| Masquol DTPA | 2.5 g |
| Cysteine hydrochloride | 0.15 g |
| Thioglycollic acid | 1.4 g |
| 22° Be strength ammonia solution | 11 cc |
| Water q.s.p. | 100 g |

60 g of the part P$_{20}$ are applied for 15 minutes to a head of hair which is initially dyed deep blond. 30 g of the part P$_6$ are then added and the mixture is left on the hair for a further 20 minutes.

After rinsing with warm water, shampooing and drying, the hair is coloured dull deep chestnut.

EXAMPLE NO. 16

The following dyeing composition is prepared:

| Part P$_{21}$: | |
|---|---|
| N,N'—(p-Aminophenyl)-N,N'—(β-hydroxyethyl)-ethylenediamine dihydrochloride | 0.7 g |
| α-Naphthol | 0.08 g |
| 2,6-Diaminopyridine | 0.03 g |
| Para-aminophenol | 0.2 g |
| Resorcinol | 0.4 g |
| 6-Methyl-3-N—(carbamylmethyl)-aminophenol | 0.1 g |
| β-Mercaptopropionic acid | 2.5 g |
| Remcopal 334 | 21 g |
| Remcopal 349 | 24 g |
| Oleic acid | 4 g |
| Trimethylcetylammonium bromide | 3 g |
| Butylglycol | 3 g |
| Absolute ethyl alcohol | 14 g |
| Masquol DPTA | 2.5 g |
| 1-Phenyl-3-methylpyrazol-5-one | 0.2 g |
| Hydroquinone | 0.2 g |
| Sodium bicarbonate | 0.35 g |
| Sodium hydroxide | 0.07 g |
| 20° Be strength ammonia solution | 11 cc |
| Water q.s.p. | 100 g |

60 g of the composition equivalent to the part P$_{21}$ are applied to a deep chestnut head of hair and left on the hair for 10 minutes.

60 g of the oxidising composition P$_2$ are then incorporated, without rinsing and whilst gently massaging the hair. After a further 20 minutes, the hair is rinsed with warm water, shampooed and dried. The head of hair is then uniformly coloured in a light chestnut shade with a dull ashen sheen.

EXAMPLE NO. 17

The following dyeing composition is prepared:

| Part P$_{22}$: | |
|---|---|
| 2-Chloro-4-amino-N—ethylaniline sulphate | 0.5 g |
| 2-Chloro-para-phenylenediamine sulphate | 0.1 g |
| 2,6 Dimethyl-4-methoxyphenol | 0.3 g |
| 2,7-Dihydroxynaphthalene | 0.2 g |
| N—Methyl-6-hydroxybenzomorpholine | 0.05 g |
| Ethyl acetylacetate | 0.05 g |
| Resorcinol | 0.05 g |
| Glycerol monothioglycollate | 0.7 g |
| Mercaptosuccinic acid | 0.9 g |
| Remcopal 334 | 22 g |
| Remcopal 349 | 22 g |
| Propylene glycol | 11 g |
| Absolute ethyl alcohol | 8 g |
| Masquol DPTA | 2.5 g |
| 1-Phenyl-3-methylpyrazol-5-one | 0.2 g |
| Sodium bicarbonate | 0.35 g |
| Sodium hydroxide | 0.07 g |
| Hydroquinone | 0.2 g |
| 22° Be strength ammonia solution | 11 cc |
| Water q.s.p. | 100 g |

60 g of this composition are applied for ten minutes to light blond hair.

After these 10 minutes, 60 g of the oxidising composition P$_2$ are added and the dyeing mixture is homogenised. After 20 minutes, the hair is rinsed, shampooed and dried.

A golden, very light blond shade with a slight ashen sheen is obtained.

EXAMPLE NO. 18

The following dyeing composition is prepared:

| Part P$_{23}$: | |
|---|---|
| N,N'—(Para-aminophenyl)-tetramethylenediamine tetrahydrochloride | 0.1 g |
| 2,6-Dimethyl-para-phenylenediamine dihydrochloride | 0.6 g |
| 2,6-Dimethylphenol | 0.05 g |
| 6-Hydroxybenzomorpholine | 0.04 g |
| Resorcinol | 0.6 g |
| Cetyl/stearyl alcohol sold under the name Alfol C 16/18 E by Messrs. CONDEA | 16 g |
| C16–C18 sodium cetyl-/stearyl-sulphate sold under the name Lanette wax E by Messrs. HENKEL | 4 g |
| Oxyethyleneated castor oil sold under the name Cemulsol B by Messrs. RHONE POULENC | 2 g |
| Thioglycol | 0.4 g |
| Glycerol monothioglycollate | 0.4 g |
| β-Mercaptopropionic acid | 1.8 g |
| Sodium bicarbonate | 0.35 g |
| Sodium hydroxide | 0.07 g |
| Ethylenediaminetetraacetic acid | 0.3 g |
| 22° Be strength ammonia solution | 11 cc |
| Water q.s.p. | 100 g |

50 g of this cream are applied for 10 minutes to a brown head of hair with a warm sheen. After this period of time, 50 g of the oxidising composition P$_4$ are incorporated and the whole is left on the hair for a further 20 minutes. The hair is then rinsed, shampooed and dried.

The head of hair is uniformly coloured chestnut with a dull sheen.

EXAMPLE NO. 19

The following dyeing composition is prepared:

| Part P₂₄: | |
|---|---|
| 2-Dimethylamino-5-aminopyridine dihydrochloride | 0.1 g |
| 2,5-Diaminopyridine dihydrochloride | 0.3 g |
| 2-Methyl-5-N—(β-hydroxyethyl)-aminophenol | 0.2 g |
| Meta-aminophenol | 0.1 g |
| Glycerol monothioglycollate | 1.8 g |
| 2-Methylresorcinol | 0.15 g |
| Cetyl alcohol | 12 g |
| 20% strength ammonium lauryl-sulphate solution | 8 g |
| Cetyl/stearyl alcohol containing 15 mols of ethylene oxide | 2 g |
| Lauryl alcohol | 4 g |
| Masquol DPTA | 2 g |
| Sodium bicarbonate | 0.4 g |
| Sodium hydroxide | 0.1 g |
| 22° Be strength ammonia solution | 14 cc |
| Water q.s.p. | 100 g |

80 g of the composition P₂₄, which is in the form of a cream, are applied to a deep blond head of hair which has been partially sensitised by a curling treatment carried out by means of a perming liquid. After an application time of 10 minutes, 40 g of the oxidising composition P₆ are added, without rinsing, and mixed with the cream which is already present on the hair. After a further application time of 20 minutes, the head of hair is rinsed, shampooed and dried.

It is coloured in an ashen light blond shade.

EXAMPLE NO. 20

The following dyeing composition is prepared:

| Part P₂₅: | |
|---|---|
| 2,4-Diamino-ortho-cresol sulphate | 0.5 g |
| 2,6-Diaminohydroquinone dihydrochloride | 0.3 g |
| 4-N—(β-Hydroxyethyl)-amino-ortho-phenylenediamine | 0.2 g |
| Hydroxyethylcellulose sold under the name CELLOSIZE WP 4400 by Messrs. CARBIDE and CARBON | 2 g |
| Ethylenediaminetetraacetic acid | 0.2 g |
| Ammonium thiolactate | 0.80 g |
| β-Mercaptopropionic acid | 0.8 g |
| 22° Be strength ammonia solution q.s.p. | pH 9.5 |
| Water q.s.p. | 100 g |

The dyestuffs are introduced in powder form into the dyeing composition at the time of use. 40 g of this composition are applied to a deep blond head of hair for 15 minutes. Without rinsing, 40 g of the oxidising composition P₂ are then added and the mixture is left on the hair for a further 15 minutes.

After this application, and after rinsing, shampooing and drying, the hair is uniformly coloured very golden light blond.

EXAMPLE NO. 21

The following dyeing composition is prepared:

| Part P₂₆: | |
|---|---|
| 2-Amino-4-methylaminophenol sulphate | 0.5 g |
| 4-N—(β-Hydroxyethyl)-amino-3-nitrophenol | 0.2 g |
| 4-N—Methylamino-1-N—(γ-aminopropyl)-aminoanthraquinone hydrochloride | 0.1 g |
| Hydroxyethylcellulose sold under the name CELLOSIZE WP 4400 by Messrs. Carbide and Carbon | 2 g |
| Ethylenediaminetetraacetic acid | 0.2 g |
| Thioglycollic acid | 2 g |
| 22° Be strength ammonia solution q.s.p. | pH 9.5 |

| Part P₂₆: | |
|---|---|
| Water q.s.p. | 100 g |

The powdered dyestuffs are introduced at the time of use.

50 g of the composition P₂₆ are applied to grey hair containing a low percentage of white hair and the composition is left on the hair for 15 minutes; after this period of time, 50 g of the oxidising composition P₂ are incorporated, without rinsing, by mixing it intimately with the composition which is already present on the hair.

After a further application time of 15 minutes, the hair is rinsed, shampooed and dried. The hair is coloured intense grey with a mauve sheen.

EXAMPLE NO. 22

The following dyeing composition is prepared:

| Part P₂₇: | |
|---|---|
| 4-Amino-N—ethyl-N—piperidinoethylaniline dihydrochloride | 0.3 g |
| 2-Methyl-5-N—(β-hydroxyethyl)-aminophenol | 0.45 g |
| Para-aminophenol | 0.40 g |
| Resorcinol | 0.05 g |
| Meta-aminophenol | 0.15 g |
| 2,4-Diaminophenoxyethanol dihydrochloride | 0.03 g |
| N—Methyl-para-aminophenol sulphate | 0.05 g |
| Thiolactic acid | 3.5 g |
| Remcopal 334 | 22 g |
| Remcopal 349 | 22 g |
| Propylene glycol | 11 g |
| Absolute ethyl alcohol | 8 g |
| Masquol DPTA | 2.5 g |
| Hydroquinone | 0.2 g |
| 1-Phenyl-3-methylpyrazol-5-one | 0.2 g |
| Sodium hydroxide | 0.07 g |
| Sodium bicarbonate | 0.35 g |
| 22° Be strength ammonia solution | 11 cc |
| Water q.s.p. | 100 g |

50 g of the composition P₂₇ are applied to deep blond hair and are left to act for 10 minutes. 50 g of the oxidising composition P₆ are incorporated, without rinsing, and the mixture is left to act for a further 20 minutes.

The hair is rinsed, shampooed and dried.

After dyeing, the hair is coloured slightly pearlescent, ashen light blond.

EXAMPLE NO. 23

The following dyeing composition is prepared:

| Part P₂₈: | |
|---|---|
| 4-(N—Tetrahydrofurfuryl)-aminoaniline dihydrochloride | 0.6 g |
| α-Naphthol | 0.04 g |
| Meta-aminophenol | 0.4 g |
| 2-Methylresorcinol | 0.05 g |
| 2-Nitro-para-phenylenediamine | 0.25 g |
| Thioglycollic acid | 1.5 g |
| Remcopal 334 | 22 g |
| Remcopal 349 | 22 g |
| Propylene glycol | 11 g |
| Absolute ethyl alcohol | 8 g |
| Masquol DPTA | 2.5 g |
| Hydroquinone | 0.2 g |
| 1-Phenyl-3-methylpyrazol-5-one | 0.2 g |
| Sodium hydroxide | 0.07 g |
| Sodium bicarbonate | 0.35 g |
| 22° Be strength ammonia solution | 11 cc |

| | -continued | |
|---|---|---|
| Part P₂₈: | | |
| Water q.s.p. | | 100 g |

50 g of the composition P$_{28}$ are applied for 20 minutes to a light chestnut head of hair possessing zones which have undergone curling by means of a perming liquid 3 months previously.

After these 20 minutes, 50 g of the oxidising composition P$_2$ are added, without rinsing, and the mixture is left on the hair for a further 15 minutes.

The hair is rinsed, shampooed and dried. It then exhibits a uniform blond coloration with an iridescent beige sheen.

EXAMPLE NO. 24

Preparation of the 4-amino-N-(β-hydroxyethy)-N-mesylaminoethylaniline dihydrochloride used in the composition P$_{17}$.

Preparation of
4-acetylamino-N-(β-mesylaminoethyl)-aniline 0.2 mol (25.2 g) of sodium sulphite is added, at ambient temperature, to a solution of 0.1 mol (32.7 g) of N-mesylaminoethyl-para-phenylenediamine sulphate in 150 ml of water, and 0.13 mol (13.17 g) of acetic anhydride is added gradually, whilst stirring. When the addition is complete, stirring is continued for one hour and the expected acetylated derivative, which has precipitated in crystalline form, is then filtered off. The product is drained, washed with water and dried in vacuo. After recrystallisation from alcohol and drying in vacuo, it melts at 130° C.

| Analysis | Calculated for C$_{11}$H$_{17}$N$_3$SO$_3$ | Found |
|---|---|---|
| C % | 48.71 | 48.71 |
| H % | 6.27 | 6.15 |
| N % | 15.50 | 15.80 |
| S % | 11.81 | 12.01 |

Preparation of
4-acetylamino-N-(β-hydroxyethyl)-N-mesylaminoethylaniline 0.037 mol (10 g) of 4-acetylamino-N-(β-mesylaminoethyl)-aniline is dissolved in 31 ml of boiling water. 7.4 g of sodium carbonate and 0.148 mol (18.5 g) of glycol bromohydrin are added, whilst stirring. After stirring for 4 hours in a boiling water bath, the reaction medium is filtered and the filtrate is then left to stand for 48 hours at 0° C. The 4-acetylamino-N-(β-hydroxyethyl)-N-mesylaminoethylaniline which has precipitated in crystalline form is filtered off. After recrystallisation from boiling water and drying in vacuo, the product melts at 118° C.

| Analysis | Calculated for C$_{13}$H$_{21}$N$_3$SO$_4$ | Found |
|---|---|---|
| C % | 49.52 | 49.80 |
| H % | 6.67 | 6.77 |
| N % | 13.33 | 13.16 |
| S % | 10.16 | 10.36 |

Preparation of
N-(β-hydroxyethyl)-N-mesylaminoethyl-para-phenylenediamine dihydrochloride monohydrate 0.0178 mol (5.6 g) of 4-acetylamino-N-(β-hydroxyethyl)-N-mesylaminoethylaniline in 12 ml of a 5N aqueous solution of hydrochloric acid is heated for 30 minutes in a boiling water bath. The water is then driven off in vacuo. The residue is kept for two hours in vacuo at 60° C. and is then obtained in crystalline form.

It is chromatographically pure.
Molecular weight calculated for

| C$_{11}$H$_{19}$N$_3$O$_3$S.2HCl.H$_2$O | | 366 |
|---|---|---|
| Molecular weight obtained by potentiometric determination | | 358 |
| Analysis | Calculated for C$_{11}$H$_{19}$N$_3$O$_3$S.2HCl.H$_2$O | Found |
| C % | 32.26 | 35.97  36.08 |
| H % | 6.31 | 6.40  6.44 |
| N % | 11.53 | 11.39  11.28 |
| Cl % | 19.50 | 19.54  19.66 |

EXAMPLE NO. 25

Preparation of
4-N-[β-(β'-hydroxyethoxy)-ethyl]-aminoaniline sulphate

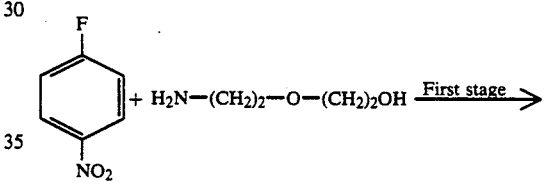

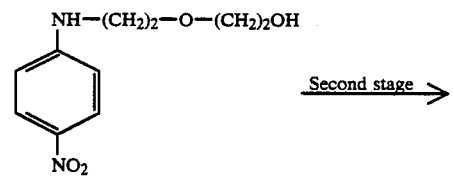

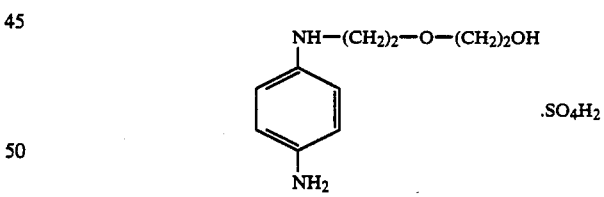

1st step: Preparation of 4-nitro-N-[β-(β'-hydroxyethoxy)-ethyl]-aniline.

0.2 mol (28.2 g) of para-fluoronitrobenzene in 84.6 ml of diglycolamine is heated for 2 and a half hours at between 110° and 120° C. After cooling the mixture, it is poured onto 300 g of crushed ice. The expected product precipitates in crystalline form. It is filtered off, washed with water and dried. After recrystallisation from ethanol and drying in vacuo, it melts at 78° C. Elementary analysis of the product obtained gives the following results:

| Analysis | Calculated for C$_{10}$H$_{14}$O$_4$N$_2$ | Found |
|---|---|---|
| C % | 53.09 | 53.20 |
| H % | 6.19 | 6.32 |

| Analysis | Calculated for $C_{10}H_{14}O_4N_2$ | Found |
|---|---|---|
| N % | 12.39 | 12.32 |

2nd step: Preparation of 4-N-[β-(β'-hydroxyethoxy)-ethyl]-aminoaniline sulphate.

7.5 g of ammonium chloride and 58.5 g of zinc powder are added to 175 ml of an aqueous-ethanolic solution (15% of water and 85% of ethanol). This mixture is heated to the reflux temperature, whilst stirring, and 0.15 mol (33.9 g) of the product obtained in the first step is then added in small portions. When the addition of the nitro derivative is complete, the reaction medium is decolorised; it is filtered at the boil, the filtrate being collected in a flask, cooled to −10° C., containing 10.5 ml of concentrated sulphuric acid and 30 ml of ethanol. The expected product precipitates in the form of a gum which crystallises rapidly. It is filtered off and washed with alcohol and then acetone. After drying in vacuo, the product melts, with decomposition, at about 157° C. After recrystallisaton from an aqueous ethanolic mixture, the product obtained is subjected to elementary analysis which gives the following results:

| Analysis | Calculated for $C_{10}H_{18}N_2O_6S$ | Found |
|---|---|---|
| C % | 40.82 | 40.65 |
| H % | 6.12 | 6.07 |
| N % | 9.52 | 9.53 |
| S % | 10.88 | 10.92–10.69 |

We claim:

1. A process for dyeing hair which comprises applying to the hair for 5 to 45 minutes a first composition containing at least one mercaptan corresponding to the formula:

$$R-SH \qquad (I)$$

in which R denotes an alkylene group bonded to a group of the formula —COOH, —CONH$_2$, —OH, —SH or —COOR', R' denoting an unsubstituted alkyl group or hydroxy-substituted alkyl group, said alkylene group being unsubstituted or substituted by one or more lower alkyl, amino or COOH groups, an ammonium, alkali metal or alkaline earth metal salt thereof or an organic or inorganic acid addition salt thereof, present in an amount greater than 1% and less than 5% by weight and subsequently without intermediate rinsing applying to the hair for 5 to 40 minutes an oxidising composition so as to develop an oxidisable dyestuff applied to the hair, said oxidisable dyestuff being a para-phenylenediamine of the formula:

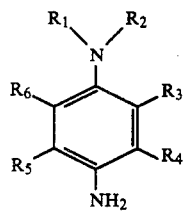

in which R$_1$ and R$_2$ independently of one another denote hydrogen; phenyl; furfuryl; tetrahydrofurfuryl; a linear or branched alkyl group which is unsubstituted or chain-terminated by a hydroxyl, alkoxy or a primary, secondary or tertiary amino group, acylamino, alkyl- or arylsulphonylamino, carbalkoxyamino, ureido, carboxyl, carbamyl in which the nitrogen atom is unsubstituted or mono- or di-substituted, sulpho, sulphonamido in which the nitrogen atom is unsubstituted or mono- or di-substituted, said alkyl groups including alkyl groups containing an oxygen or nitrogen atom and alkyl groups substituted by other hydroxy or amino groups; or R$_1$ and R$_2$ together form, with the nitrogen atom to which they are attached, a piperidino or morpholino ring; and R$_3$, R$_4$, R$_5$ and R$_6$ independently of one another denote hydrogen, halogen, linear or branched alkyl which is unsubstituted or substituted by one or more OH, amino or alkoxy groups, or a group OZ, Z denoting alkyl, hydroxyalkyl, alkoxyalkyl, acylaminoalkyl, carbalkoxyaminoalkyl, mesylaminoalkyl, ureidoalkyl, aminoalkyl or mono- or di-alkylaminoalkyl, with the proviso that if R$_2$ denotes phenyl, R$_1$, R$_3$, R$_4$, R$_5$ and R$_6$ denote hydrogen, and that if R$_1$ and R$_2$ are both different from hydrogen, R$_3$ and R$_6$ both denote hydrogen, and that if R$_1$ and R$_2$ simultaneously denote hydrogen, at least two of the substituents R$_3$, R$_4$, R$_5$ and R$_6$ are different from hydrogen; or an organic or inorganic acid salt thereof; a para-aminophenol, a 2,5-diamino pyridine, an amino benzomorpholine, or a N,N'-diarylalkylenediamine in which the aryl groups are substituted in the para position by an OH, amino or amino substituted by alkyl, unsubstituted or substituted on the nucleus by alkyl or halogen, and in which the alkylene group is uninterrupted or interrupted by O or N or is unsubstituted or substituted by OH or an alkyl group, the nitrogen atoms carried by the alkylenediamine groups being unsubstituted or substituted by an alkyl, hydroxyalkyl or aminoalkyl group, present in an amount of 0.005 to 10% by weight, or a 4,4'-diaminodiphenylamine, a 4-hydroxy 4'-aminodiphenylamine or a 4,4'-dihydroxydiphenylamine present in an amount of 0.005 to 4% by weight, or pyrogallol, 1,2,4-trihydroxybenzene, 1,3,5-trihydroxybenzene, 1,4,5-trihydroxynaphthalene, 2,4,5-trihydroxytoluene, alphajuglone, triaminobenzene, di- or triaminophenol, polyaminopolyhydroxybenzene present in an amount of 0.01 to 8% by weight.

2. Process according to claim 1 in which said oxidisable dyestuff is present in the oxidising composition.

3. Process for dyeing hair of claim 1 which comprises applying a first composition containing at least the said mercaptan present in an amount greater than 1% and less than 5% by weight and at least one of the said oxidisable dyestuff, and, subsequently, without intermediate rinsing, applying an oxidising composition so as to develop the dyestuff on the hair.

4. Process according to claim 1 in which the said mercaptan is present in an amount from 1.5 to 3.5% by weight.

5. Process according to claim 1 or 3 in which all or part of the said mercaptan is introduced into the first composition just before use.

6. Process according to claim 1 or 3 in which the oxidising composition contains 0.1 to 12% by weight of hydrogen peroxide.

7. Process according to claim 1 in which a coupler is present in an amount of 0.005 to 10% by weight.

* * * * *